(12) United States Patent
Fischer et al.

(10) Patent No.: US 7,527,975 B2
(45) Date of Patent: May 5, 2009

(54) DETERMINATION OF HIGH LIPOPHILICITY VALUES

(75) Inventors: Holger Fischer, Grellingen (CH);
Manfred Kansy, Freiburg (DE); Bjoern Wagner, Binzen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 209 days.

(21) Appl. No.: 11/375,903

(22) Filed: Mar. 15, 2006

(65) Prior Publication Data

US 2006/0211121 A1    Sep. 21, 2006

(30) Foreign Application Priority Data

Mar. 21, 2005    (EP)    ................. 05102211

(51) Int. Cl.
*G01N 33/92*    (2006.01)
(52) U.S. Cl. .......................... 436/60; 436/71
(58) Field of Classification Search ............ 436/60, 436/71; 702/22; 210/644
See application file for complete search history.

(56) References Cited

U.S. PATENT DOCUMENTS

2002/0161528 A1* 10/2002 Lombardo et al. ............ 702/22
2007/0205155 A1*  9/2007 Babcock et al. ............. 210/644

FOREIGN PATENT DOCUMENTS

EP          1232792       8/2002
WO    WO 2005/095950    10/2005

OTHER PUBLICATIONS

Zhu, Chengyue et al., A comparative study of artificial membrane permeability assay for high throughput profiling of drug absorption potential, 2002, Eur. J. Med. Chem., 37, 399-407.*
Cserhati, T., Lipophilicity Determination of some 3,5-Dinitro-Benzoic-Acid Esters on Unimpregnated Cellulose Layer, 1984, Chromatographia, vol. 18, No. 1, 318-322.*
Kansy, Manfred et al., Physicochemical High Throughput Screening: Parallel Artificial Membrane Permeation Assay in the Description of Passive Absorption Processes, 1998, Journal of Medicinal Chemistry, vol. 41, No. 7, 1007-1010.*
Alegria, Antonio E. et al., Membrane-Buffer Partition Coefficients of Semiquinones using the Spin -broadening Technique, 1993, J. Chem. Soc. Faraday Trans., 89(20), 3773-3777.*

(Continued)

*Primary Examiner*—Walter D Griffin
*Assistant Examiner*—Christine T Mui
(74) *Attorney, Agent, or Firm*—George W. Johnston; Dennis P. Tramaloni

(57) ABSTRACT

The present invention relates to a novel method for determining the lipophilicity of a compound of interest comprising a) providing a layer, b) impregnating said layer with a solvent A, c) applying a dissolved compound of interest on the impregnated layer, d) adding a solvent B, e) removing the solvent B after the distribution equilibrium has been reached, and f) determining the quantity of the compound of interest in at least one of the solvent phases.

12 Claims, 8 Drawing Sheets

OTHER PUBLICATIONS

Hitzel, et al, *Pharma Res*, 17(11) 1389-95 (2000).
Takacs-Novak, K. et al, *Jour. of Pharma & Biomedical Analysis*, 14(11) 1405-1413 (1996).
Wohnsland, F. et al, *Jour. of Med. Chem*, 44;6 923-930, (2001).
Wong, K. et al, *Jour. of Pharma Sci.*, 93:4 916-931 (2004).
Kerns, E. et al, *Jour of Chromoatography B*, 791:1-2, 381-388 (2003).
Abraham, M. et al, *Phys. Org. Chem.*, 7:712-716 (1994).
Berthod, A, *Jour. of Chromatography*, 1037 (1-2) p. 3-14 (2004).
Chopineaux-Courtois, V. et al *J. Am. Chem. Soc.*, vol. 121, 1743-1747 (1999).
Biagi, G. et al *Jour. Of Chromatography*, vol. 662, 341-361 (1994).
Sarbu, C. et al, *Jour. Of Chromatography*, vol. 917, 361-366 (2001).

\* cited by examiner

A)

5 B)

A)

B)

A)

B)

C

DETERMINATION OF HIGH LIPOPHILICITY VALUES

PRIORITY TO RELATED APPLICATIONS

This application claims the benefit of European Application No. 05102211.9, filed Mar. 21, 2005, which is hereby incorporated by reference in its entirety.

FIELD OF THE INVENTION

The present invention provides a method for determination of high, medium and low lipophilicity values.

BACKGROUND OF THE INVENTION

Lipophilicity is an important molecular property in drug discovery. The exact knowledge of drug lipophilicity is useful for correlation with pharmaceutical processes such as membrane permeation, solubility, volume of distribution, metabolic stability and protein binding. Lipophilicity is expressed either by log P (octanol-water Partition coefficient for neutral species) or log D (octanol-water Distribution coefficient for charged molecules).

Usually, the lipophilicity is determined by the conventional shake-flask method (M. M. Abraham, H. S. Chadha, J. P. Dixon, and A. J. Leo. *Hydrogen bonding. Part 9. The partition of solutes between water and various alcohols*. Phys. Org. Chem. 7:712-716 (1994). When performed manually, this method is very time consuming (only 2-5 compounds per day). However, the number of compounds produced in drug discovery increased dramatically due to rapid analogue synthesis and combinatorial chemistry. This situation requests for a fast and efficient method for determining the lipophilicity of compounds.

Further, the methods of the prior art do not work with low soluble compounds. Since 2002 about 35% of the log D measurements were failed due to the precipitation of compounds in the reference solution or low sample concentrations in the aqueous phase (source: RODIN and SPC database, 2004). On the other hand, there is a need for high throughput measurements of log D>4, especially for drug targets where high lipophilicity is required.

Therefore, there is a requirement for a method which is fast and which allows the determination of lipophilicity of low soluble compounds.

SUMMARY OF THE INVENTION

The present invention relates to a method of determining the lipophilicity of a compound of interest comprising:
a) providing a layer,
b) impregnating said layer with a solvent A,
c) applying a compound of interest on the impregnated layer,
d) adding a solvent B,
e) removing the solvent B after the distribution equilibrium has been reached, and
f) determining the quantity of the compound of interest in at least one of the solvent phases.

Alternatively, the present invention relates to a method of determining the lipophilicity of a compound of interest comprising:
a) impregnating a layer with a solvent A,
b) applying a compound of interest on the impregnated layer,
c) adding a solvent B,
d) removing the solvent B after the distribution equilibrium has been reached, and
e) determining the quantity of the compound of interest in at least one of the solvent phases.

Preferably, the quantity of the compound of interest is determined in the solvent phase sticking to the layer.

Figure 1:
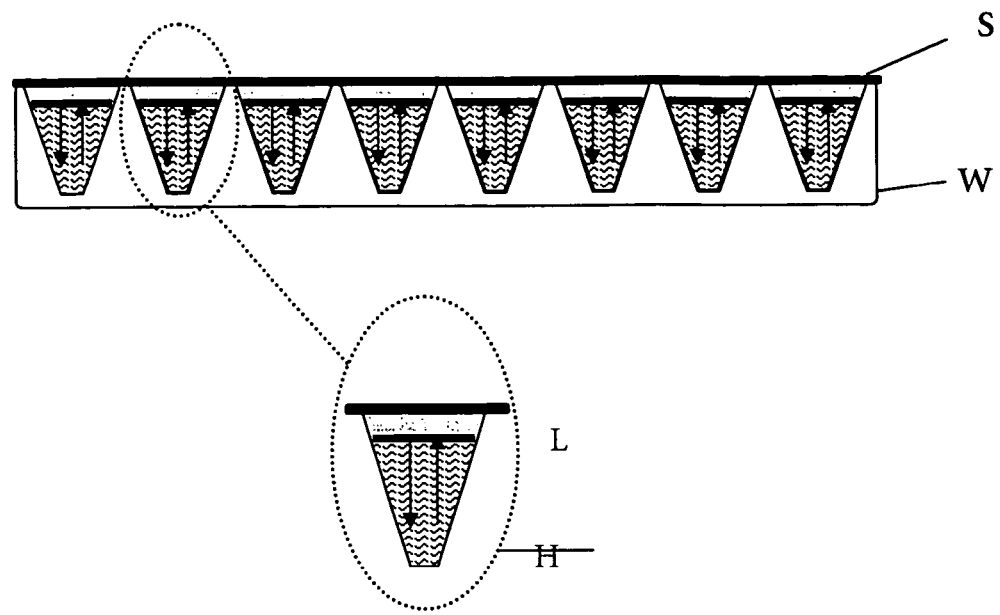
FIG. 1 shows schematically a method of the prior art. The compound of interest is dissolved in a suitable solvent and added with a hydrophilic buffer (H) in a multi-well plate (W). A lipophilic solvent (L) is added to the buffer. The plate is sealed (S) and the plate is shaken till an equilibrium of distribution is reached. Then the aqueous phase is removed and the quantity of the compound of interest in the hydrophilic buffer is determined. Due to the small volumes the separation of the phases is difficult and often not satisfying.

LIST OF REFERENCE NUMBERS 11 linear cuvette array
12 cuvette
13 cuvette
14 cuvette
15 web
16 web
17 upper chamber
18 lower chamber
19 rib
21 latch
22 latch 23 open low end
24 open top end
25 bottom wall
26 opening
27 inner surface of bottom wall 25
29 rib
31 array
32 cuvette
33 neighboring cuvette
34 neighboring cuvette
35 single web
36 single web
37 upper chamber
38 lower chamber
41 rib
42 rib
43 lower top end
44 open top end
45 bottom wall
46 opening
51 two-dimensional cuvette array
52 cuvette holder
53 matrix array of openings
54 opening (for receiving cuvettes)
61 layer
71 layer
81 two-dimensional cuvette array
82 cuvette holder
83 holder plate
85 standard holder plate for a standard multiwell plate
91 upper cuvette
92 lower cuvette

DEFINITIONS

All references cited herein are referenced in their entirety.

The term "layer" as used herein refers to a carrier for a solvent, whereby the layer is able to completely absorb the solvent. The term "completely absorbed" means that the solvent applied to the layer (i.e. Solvent A) is bound to the layer and may not leak into the other phase (i.e. Solvent B).

The term "non-polar solvent" as used herein refers to a hydrophobic solvent. Non-polar solvents are immiscible, or hardly miscible with polar solvents such as for example water. A lipophilic compound has usually the tendency to be more soluble in a non-polar solvent than in a polar solvent. The dielectric constant of a non-polar solvent is usually lower than that of water. Examples of a hydrophobic solvent are organic solvents such as i.e. octanol or aliphatic hydrocarbons (dodecane, hexadecane, chloroform, methylenchlorid or other halogenized hydrocarbons).

The term "hydrophilic solvent" or "polar solvent" as used herein refers to a solvent that molecules whose electric charges are not equally distributed and are therefore electronically charged. Polar solvents are immiscible or hardly miscible with non-polar or hydrophobic solvents. Polar or ionizable compounds have the tendency to be more soluble in polar solvents. The polar solvent may be for example a hydrophilic buffer solution which could consist of a buffer salt (i.e. aqueous solutions of phosphate or TAPSO salts buffered at about pH 7.4) in water with high buffer capacity within the pH range of interest. The pH of interest may be in the range between pH 0 to 14, preferably the pH is about 7.4. Examples of Buffer may include compositions of organic or anorganic salts which can stabilize pH values e.g., phosphate buffer. Borate, tarte, phthalate—or organic buffers e.g, TAPSO, MOPSO, HEPES, TRIS, are known to those of ordinary skill in the art.

A buffer, as defined by Van Slyke [1], is "a substance which by its presence in solution increases the amount of acid or alkali that must be added to cause unit change in pH", by maintaining a constant concentration of hydrogen ions within a physiological range. For example, the pH of mammalian blood is maintained close to about 7.38 by buffer systems such as $H_2PO_4^- <=> HPO_4^{2-}$, $CO_2 <=> H_2CO_3$, $H_2CO_3 <=> HCO_3^-$. A buffer salt, as used herein, such as aqueous solutions of phosphate or TAPSO salts buffers at about pH 7.4. Other buffers which could be used are readily determinable/known by one of ordinary skill in the art.

The term "distribution equilibrium" as used herein refers to the equilibrium of distribution between the polar solvent and the non-polar solvent for compounds of interest after a specific time. Preferably, the distribution equilibrium is achieved between 0.1-24 h, more preferably it is achieved within 2 h.

The term "hydrophobic layer" as used herein refers to a carrier for non-polar solvent. Preferably, the hydrophobic layer is a hydrophobic membrane. Such membranes may be formed as a mesh out the hydrophobic material or a layer with pores. Preferably, the pore size or mesh size is in the range between 0.01-100 µm. The hydrophobic membrane carrier material comprises but is not limited to PVDF, PTFE, cyclic olefin copolymer (COC), PP or PC.

The term "hydrophilic layer" as used herein refers to a carrier for polar solvent. Preferably, the hydrophilic layer is a hydrophilic membrane. Such a membrane may be formed as a mesh of hydrophilic material or as a layer with pores. Preferably, the pore size or mesh size is in the range between 0.01-100 µm. The hydrophilic carrier material comprises but is not limited to cellulose acetate, glass fibres, hydrophilic polyvinylidendifluoride (PVDF), hydrophilized polycarbonate and other hydrophilized filter material.

DETAILED DESCRIPTION OF THE INVENTION

The present invention relates to a method of determining the lipophilicity of a compound of interest comprising:
a) providing a layer,
b) impregnating said layer with a solvent A,
c) applying a compound of interest on the impregnated layer,
d) adding a solvent B,
e) removing the solvent B after the distribution equilibrium has been reached, and
f) determining the quantity of the compound of interest in at least one of the solvent phases.

Preferably, the quantity of the compound of interest is determined in the solvent phase sticking to the layer.

The compound of interest may be any chemical or biological compound. The compound of interest may be for example an organic compound, a protein, a peptide or a nucleic acid. An organic compound may include also organic-inorganic molecules. The term organic-inorganic molecule as used herein refers to an organic molecule in which at least one inorganic atom is bound to a carbon atom. An inorganic atom may i.e. a metal atom such as i.e. silicon (Si) or germanium (Organometallics, i.e. Si or Ge bioisoester of organic molecules).

The compound of interest may be solid or liquid. The compound of interest may be dissolved in a suitable solvent as for example DMSO (dimethyl sulfoxide). The compound of interest may a lipophilic compound or a hydrophilic compound. A suitable solvent for a hydrophilic compound is preferably a polar solvent; a suitable solvent for a lipophilic compound is preferably a non polar solvent.

The provided layer has a plurality of hollows. These hollows may be pores, cavities, holes or slots. The hollows may be formed by the carrier material, such as it is the case e.g. with fibers which form a mesh. The hollows may also be created e.g. by penetrating the layer with ions. Preferably, the layer is permeable.

The layer may be for example a mesh or a membrane (e.g. Westran Clear Signal membrane foil (Whatman), Immobilon-P PVDF (Millipore), PVDF-Plus, Transfer Membrane (Koma Biotech)). Preferably, the layer is a membrane. If the solvent is non-polar the carrier material is preferably hydrophobic such as i.e. polyvinyldenfluorid (PVDF), polytetrafluorethylen (PTFE), cyclic olefin copolymer (COC), polypropylene (PP) or polycarbonate (PC). If the solvent is polar the carrier material is preferably lipophilic such as i.e. celluloseacetate, glass fibres, hydrophilic polyvinylidendifluoride (PVDF), hydrophilized polycarbonate and other hydrophilized filter material.

Solvent A may be a non-polar or polar solvent. Solvent B may also be a non-polar or polar solvent. Solvent A is immiscible or hardly miscible with solvent B. If solvent A is a non-polar solvent, solvent B is a polar solvent, if solvent A is a polar solvent, solvent B is a non-polar solvent.

The layer may be impregnated (i.e., filling the layer, for example filling filter pores at the membrane layer, with solvent) by applying the solvent to the layer whereby the layer is able to absorb the solvent completely. The solvent may be applied i.e. by a dispenser. Further methods are known in the art such as for example robotic liquid handling system, which allows to dispense $0.1\,\mu l$ -$50\,\mu l/cm^2$ of the organic modifier on the surface of the layer which may be a filter membrane.

The quantity of the compound of interest in the solvent (solvent A or solvent B) may be determined by methods comprising but not limited to the group consisting of UV- and/or mass spectroscopy, capillary electrophoresis (CE) and high pressure liquid chromatography (HPLC).

Preferably, the layer is attached at the bottom of a tube. A tube comprises but is not limited to, a cuvette, a well and a multiwell-plate. Preferably, said tube to which the layer is attached to is the tube as described in the European Patent application EP 1232792, which is herewith fully incorporated as reference. More preferably, the tube to which the layer is attached to is the tube described in EP 05111522.8 which is herewith fully incorporated as reference.

Figure 5:
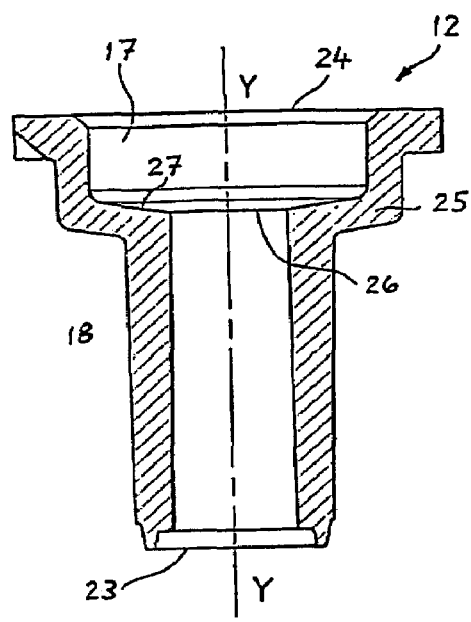
FIG. 5 shows a cross-sectional view of one of the cuvettes 12 of the linear cuvette array 11 in FIG. 4. A) without layer, B) with attached layer 61.
Figure 5:
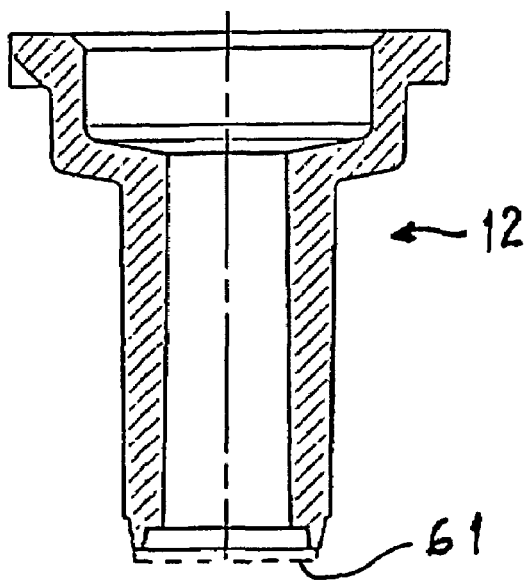

The preferred cuvette to which the layer is attached to, has an upper chamber 17 and a lower chamber 18 which have a common symmetry axis Y-Y which passes through the centers of both chambers. Upper chamber 17 and lower chamber 18 have each a substantially cylindrical shape. The cross-section of upper chamber 17 at the central part thereof is larger than the cross-section of lower chamber 18 (FIG. 5).

This cuvette has a lower chamber 18 with an open lower end 23 and an upper chamber 17 with an open top end 24 and an annular bottom wall 25. This bottom wall has a central circular opening 26 which connects said upper chamber 17 with lower chamber 18 (FIG. 5).

The inner surface 27 of bottom wall 25 is part of a conical surface the cross-section of which forms an angle of about 80 degrees with the symmetry axis Y-Y of the cuvette, so that there is an abrupt change of cross-section between said upper chamber 17 and said lower chamber 18.

Following materials are examples of materials which can be used to manufacture a cuvette: celluloseacetate, polycarbonate, polyvinylidene fluoride (PVDF), polysulfones, polystyrene, polypropylene (PP), cyclic olefin copolymer (COC). Materials with similar shrinkage coefficient (in connection with injection molding) and melting properties may also be used for manufacturing a tube.

Figure 4:
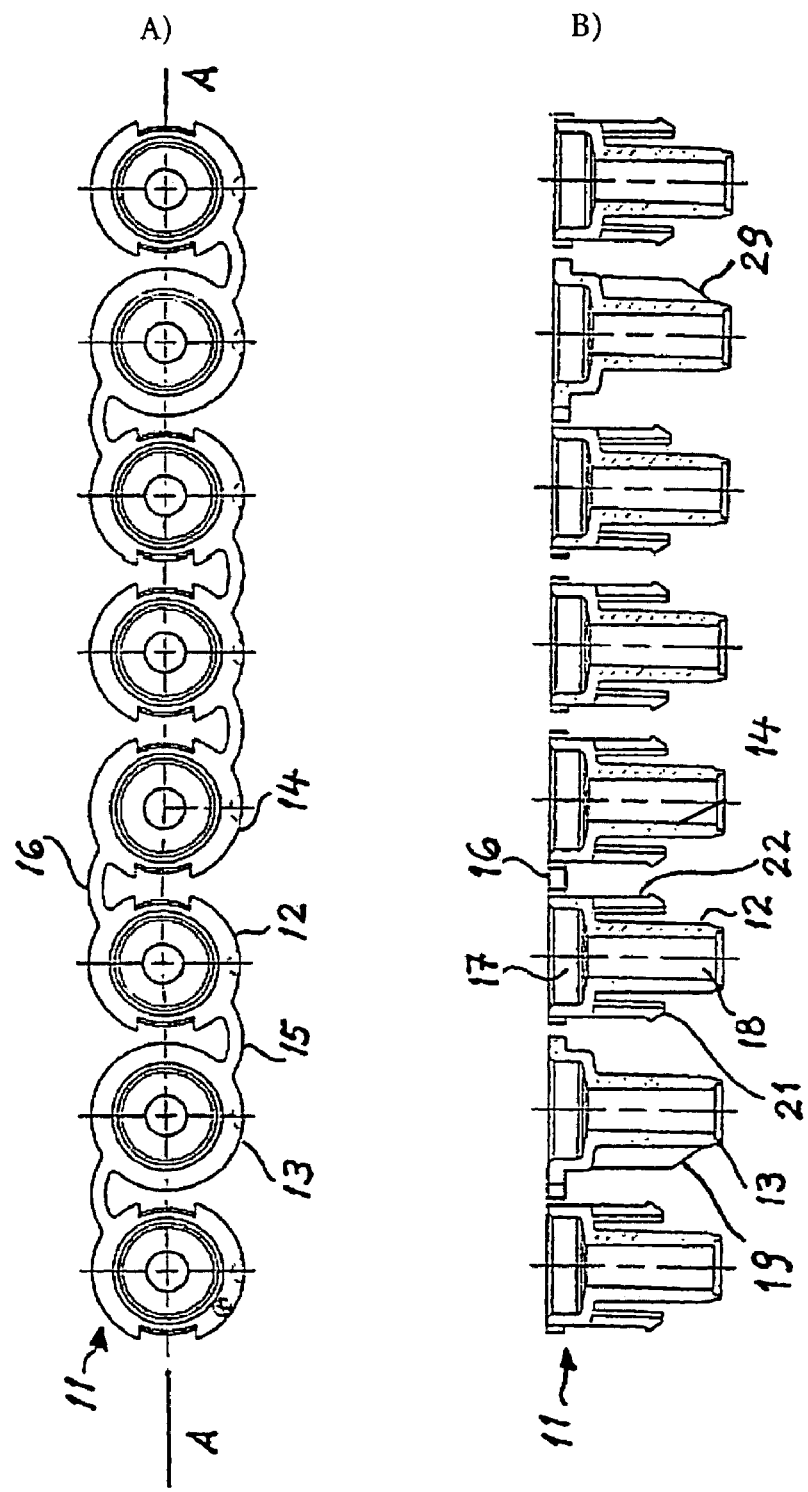
FIG. 4 shows a linear cuvette array 11. A) top view of the cuvette array, B) cross-section through a plane A-A of the cuvette array in A).

Preferably, the cuvette is part of an array 11 (FIG. 4). Each of the cuvettes in the array has the same shape and dimensions, and neighboring cuvettes are connected to each other by a single web 15, 16. Each of these single webs 15, 16 has a curved shape.

The symmetry axis Y-Y of every cuvette 12 which forms part of array 11 of cuvettes lies substantially in one and the same plane A-A which is a symmetry plane of cuvette array 11. The upper part of an intermediate cuvette 12 of array 11 is connected by a first single web 15 to a neighboring cuvette 13 which lies on one side of intermediate cuvette 12 and is connected by a second single web 16 to a neighboring cuvette 14 which lies on the opposite side of intermediate cuvette 12. First single web 15 and second single web 16 lie on opposite sides of said symmetry plane A-A.

Webs 15, 16 are flexible and therefore facilitate the insertion of the cuvettes in a cuvette holder in spite of variations of the length of cuvette array 11 which are due to different shrinkage coefficients of the different materials used for manufacture of cuvette arrays 11 by injection molding.

Figure 8:
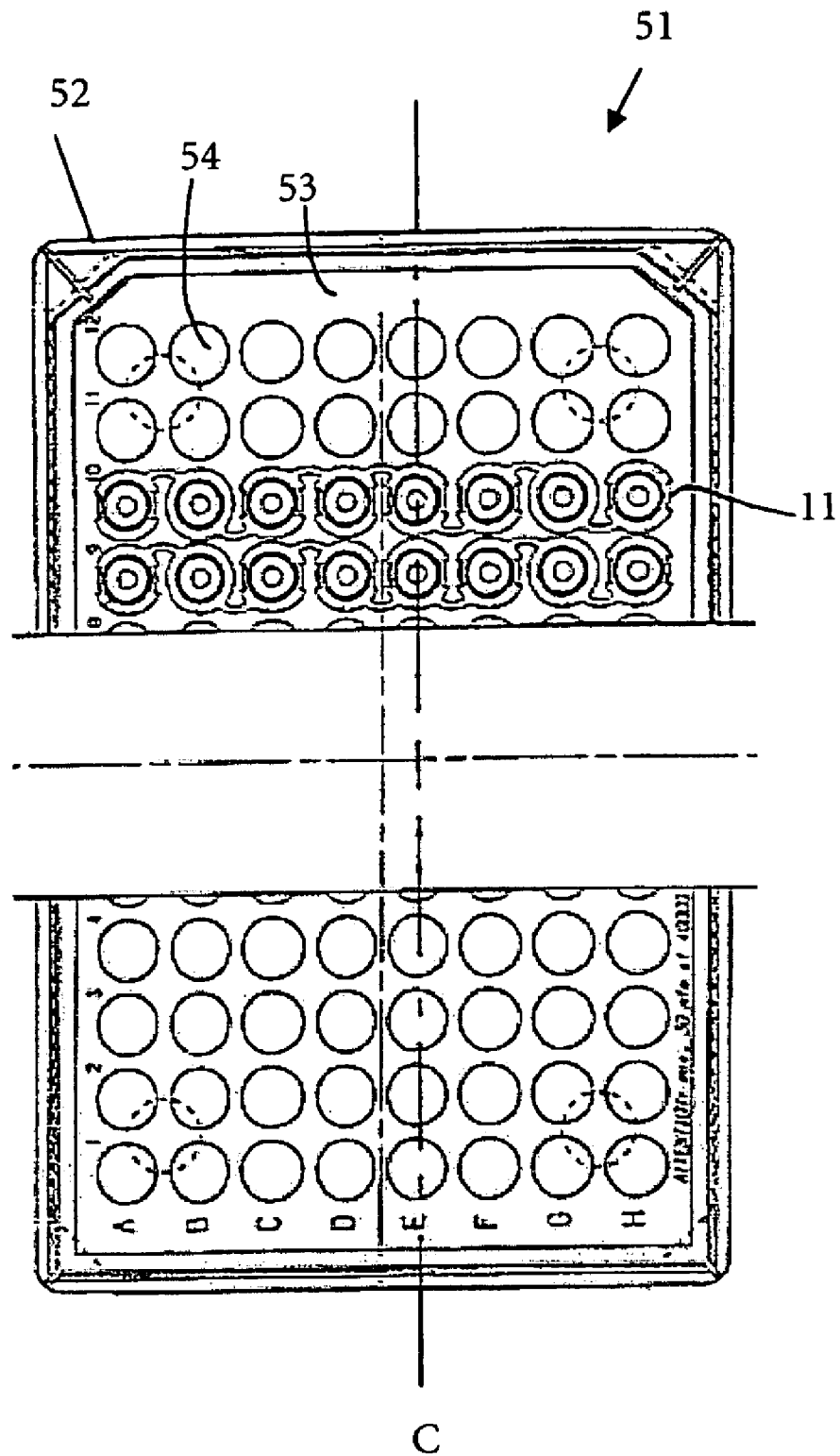
FIG. 8 shows a top view of a two-dimensional cuvette array 51 with a cuvette holder 52, a matrix array 53 and opening for cuvettes 54, in the two dimensional cuvette array 51 are two linear cuvette arrays 11 inserted.

Some of cuvettes of cuvette array 11 have latches 21 and 22 (FIG. 4B) which are an integral part of the cuvette and which serve for removably connecting the cuvette to a cuvette holder 52. In another preferred embodiment cuvette holder 52 is of substantially rectangular shape and has four centering ribs located each on the outer surface of one of the corners of cuvette holder 52 (FIG. 8).

Some of the cuvettes of cuvette array 11 have radially oriented ribs 19, 29 (FIG. 4B) which serve for accurately positioning the cuvette into an opening of cuvette holder 32.

The cuvette array 11 is made by injection molding of a selected first plastic material which is particularly suitable for being used in combination with a second selected material of which a layer is made. This layer is adapted to be closely attached to each cuvette of the array of cuvettes for covering at least one opening of each cuvette.

The injection molding apparatus for manufacturing the cuvette array is preferably so configured and dimensioned that injection molding of different materials having different shrinkage coefficients can be carried out with one and the same apparatus.

Following materials are examples of materials which can be used to manufacture cuvette array 11: celluloseacetate, polycarbonate, polyvinylidene fluoride (PVDF), polysulfones, polystyrene, polypropylene (PP). Materials with similar shrinkage coefficient (in connection with injection molding) and melting properties may also be used for manufacturing cuvette array 11.

The attachment of the layer to each cuvette can be effected e.g. by gluing the layer and the cuvette or by a welding process. The layer attached to each individual cuvette is attached only to this individual cuvette and has no connection with any other cuvette or with a foil attached to a different cuvette.

The attachment of the layer to the cuvette must ensure a medium tight connection (liquid tight connection) of these components. As known to one of ordinary skill in the art, medium-tight is a generic term for liquid/gas or air-tight for the welding contour. A liquid-tight connection means a connection which does not allow liquid to diffuse into the welding contour.

Figure 7:
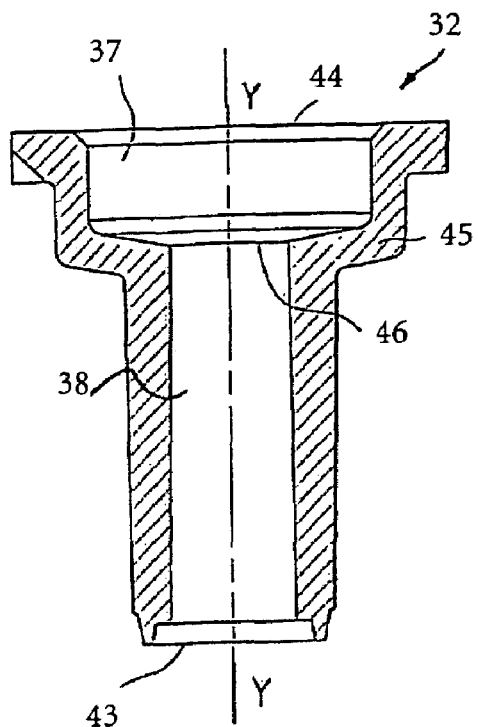
FIG. 7 shows a cross-sectional view of one of the cuvettes 32 of the linear cuvette array 31 in FIG. 6. A) without layer, B) with attached layer 71.
Figure 7:
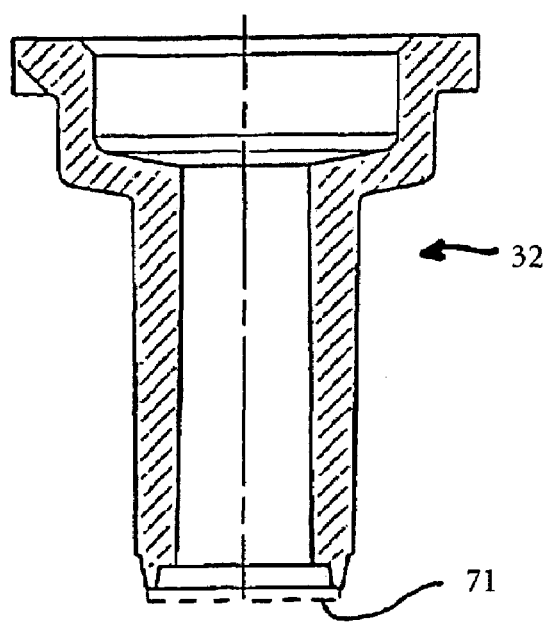

A more preferred tube to which the layer is attached is a cuvette which has an upper chamber 37 and a lower chamber 38 and a common symmetry axis Y-Y which passes through the centers of both chambers. Upper chamber 37 and lower chamber 38 have each a substantially cylindrical shape. The cross-section of upper chamber 37 at the central part thereof is larger than the cross-section of lower chamber 38 (FIG. 7A).

Lower chamber 38 has an open lower end 33. Upper chamber 37 has an open top end 34 and an annular bottom wall 35. This bottom wall has a central circular opening 36 which connects said upper chamber 37 with lower chamber 38.

The inner surface of bottom wall 45 is part of a conical surface the cross-section of which forms an angle of about 80 degrees with the symmetry axis Y-Y of the cuvette, so that there is an abrupt change of cross-section between said upper chamber 37 and said lower chamber 38.

The cuvette array 31 is made by injection molding of a selected first plastic material which is particularly suitable for being used in combination with a second selected material of which a layer is made. This layer is adapted to be closely attached to at least one cuvette of the array of cuvettes for covering at least one opening of the cuvette. The same plastic material may be used for said first plastic material and said second plastic material.

The attachment of layer to one or more cuvettes can be effected e.g. by gluing the layer and the one or more cuvettes or by a welding process. The layer attached to one individual cuvette is attached only to this individual cuvette and has no connection with any other cuvette or with a layer attached to a different cuvette.

The attachment of the layer to the cuvette must ensure a medium tight connection (liquid and/or gas tight connection) of these components. As known to one of ordinary skill in the art, medium-tight is a generic term for liquid/gas or air-tight for the welding contour. A liquid-tight connection means a connection which does not allow liquid to diffuse into the welding contour. the term "gas-tight" means that the welding contour between well and membrane has to be sufficiently tight for gas/air in order to prevent and avoid diffusion of gas and liquids into the area of the welding contour, as such diffusion could influence the results of measurement.

Figure 6:
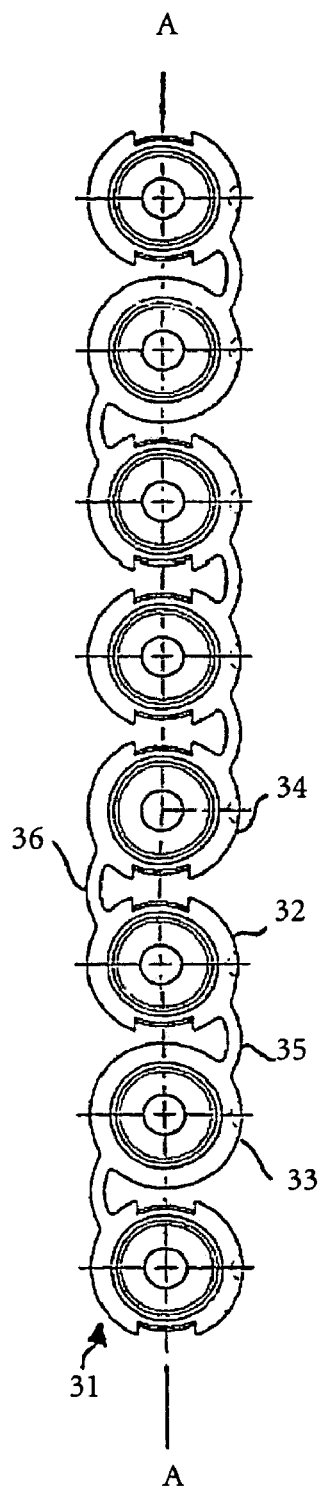
FIG. 6 shows a linear cuvette array 31. A) top view of the cuvette array, B) cross-section through a plane A-A of the cuvette array in A).
Figure 6:
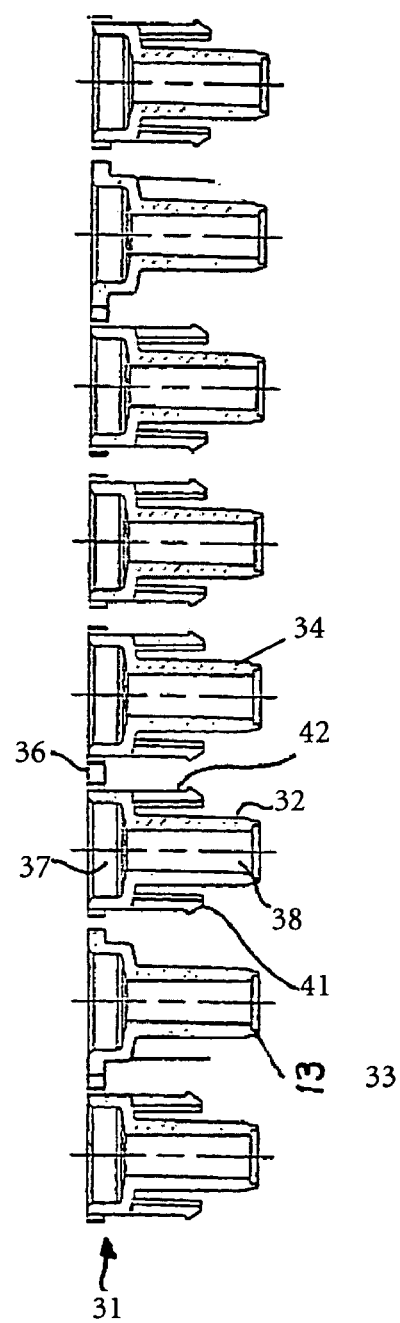

Every cuvette of array 31 has the same shape and dimensions and neighboring cuvettes are connected to each other by a single web 35, 36. Each of these single webs 35, 36 is flexible and has a curved shape (FIG. 6).

The symmetry axis Y-Y of every cuvette 32 which forms part of array 31 of cuvettes lies substantially in one and the same plane A-A which is a symmetry plane of cuvette array 31. The upper part of an intermediate cuvette 32 of array 31 is connected by a first single web 35 to a neighboring cuvette 33 which lies on one side of intermediate cuvette 32 and is connected by a second single web 36 to a neighboring cuvette 34 which lies on the opposite side of intermediate cuvette 32.

The single webs 35, 36 are flexible and therefore facilitate the insertion of the cuvettes in a cuvette holder, e.g. cuvette holder 52, in spite of variations of the length of cuvette array 31 which are due to different shrinkage coefficients of the different materials used for manufacture of cuvette arrays 31 by injection molding. These single webs 35, 36 may lie on either of two opposite sides of the plane A-A (FIG. 5).

At least two of the cuvettes of the array 31 have means which are an integral part of the cuvette for removably connecting the cuvettes to cuvette holder. Preferably, these connecting means are latches 41 and 42. In a preferred embodiment the cuvette holder is of substantially rectangular shape and has four centering ribs located each on the outer surface of one of the corners of cuvette holder like the cuvette holder 52 in FIG. 8.

Preferably, the distribution of cuvettes with connecting means over the array is equitable. If two cuvettes have connecting means preferably the first and the last cuvettes has each connecting means, or second and the last but one cuvette has each connecting means, or the third and the last but two cuvette has each connecting means, and so on.

In a preferred embodiment, in array of eight cuvettes, the first cuvette, the third cuvette, the fourth, the fifth, the sixth and the eighth cuvette has each connecting means.

As can be appreciated from FIG. 8, a two-dimensional array 51 of cuvettes according to the cuvette holder 52 having a matrix array 53 of openings 54 for receiving cuvettes 12, 32 of at least one linear cuvette array 11, 31 having the above described features. Each of the cuvettes 12, 32 of cuvette array 11, 31 has a shape and dimensions that snugly fits into one of openings 54 of cuvette holder 52.

Figure 9:
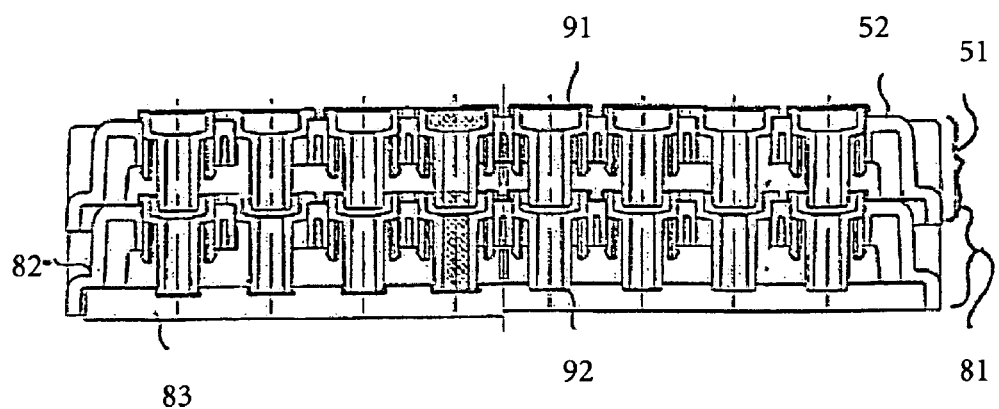
FIG. 9 shows a cross-sectional representation of stacked two-dimensional cuvette arrays 51 and 81.

As shown by FIG. 9, two or more two-dimensional cuvette array 51and 81 each of which has the structure described above with reference to FIG. 8 can be stacked on each other to form a three-dimensional cuvette array. The components of such an array are so configured and dimensioned that cuvettes having the same relative position in their respective holders are accurately positioned one above the other with coincidence of their symmetry axis, one of said cuvettes taking the position of an upper cuvette 91 and the other cuvette taking the position of a lower cuvette 92. In a preferred embodiment a portion of the lower part of each upper cuvette 91 lies within the upper chamber of the corresponding lower cuvette 92 and the lower end of the upper cuvette 91 is at a predetermined distance, as given by the dimensions of the holder plate, from the bottom wall of the upper chamber of the lower cuvette 92.

Figure 10:
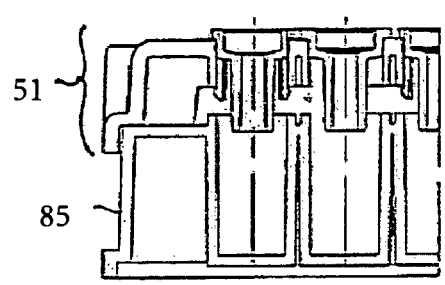
FIG. 10 shows a cross-sectional representation of a two-dimensional cuvette array 51 stacked onto a standard analysis multiwell plate 85.

As shown by FIG. 10, a two-dimensional cuvette array 51 which has the structure described above with reference to FIG. 8 can be stacked also on a standard holder plate 85 for a standard multiwell plate.

One embodiment of the present invention relates to a method of determining the lipophilicity of a lipophilic compound of interest comprising:

a) providing a hydrophobic layer,
b) impregnating said layer with a non-polar solvent,
c) applying the compound of interest on the impregnated layer,
d) adding a hydrophilic solvent,
e) removing the hydrophilic solvent after the distribution equilibrium has been reached, and
f) determining the quantity of the compound of interest in the lipophilic solvent phase sticking to the hydrophobic layer.

A lipophilic compound of interest may be for example polycyclic aromatic or aliphatic hydrocarbons, fat soluble vitamins, hydrophobic drugs like fungicides, halogen-containing aromatic or aliphatic hydrocarbons, nitrogen and oxygen containing aromatic or aliphatic hydrocarbons.

The non-polar solvent is immiscible or hardly miscible with the polar solvent. The non-polar solvent is a hydrophobic solvent, preferably hydrophobic organic solvents and is preferably selected from the group consisting of octanol and aliphatic hydrocarbons, with octanol (octan-1-ol) being more preferred. The preferred polar solvent is water or a buffer.

Another embodiment of the present invention relates to a method of determining the lipophilicity of a hydrophilic compound of interest comprising:

a) providing a hydrophilic layer,
b) impregnating said layer with a polar solvent,
c) applying the compound of interest on the impregnated layer,
d) adding a non-polar solvent, e) removing the non-polar solvent, and f) determining the quantity of the compound of interest in the hydrophilic phase sticking to the hydrophilic layer.

The non-polar solvent is immiscible or hardly miscible with the polar solvent. The preferred non-polar solvent is octanol (octan-1-ol). The preferred polar solvent is water or a buffer.

The present invention further pertains the use of a layer impregnated with a solvent for determination of lipophilicity of a compound of interest.

The layer may be a hydrophobic or hydrophilic layer. The solvent may be a non-polar (hydrophobic) or polar (hydrophilic) solvent. If the solvent is a non-polar solvent the layer is preferably hydrophobic. If the solvent is a polar solvent, the layer is preferably hydrophilic.

The compound of interest may be any chemical or biological compound. The compound of interest may be for example an organic compound, a protein, a peptide or a nucleic acid. An organic compound may include also organic-inorganic molecules. The term organic-inorganic molecule as used herein refers to an organic molecule in which at least one inorganic atom is bound to a carbon atom. An inorganic atom may i.e. a metal atom such as i.e. silicon (Si) or germanium (Organometallics, i.e. Si or Ge bioisoester of organic molecules).

The compound of interest may be solid or liquid. The compound of interest may be dissolved in a suitable solvent as for example DMSO (dimethyl sulfoxide). A suitable solvent for a hydrophilic compound is preferably a polar solvent; a suitable solvent for a lipophilic compound is preferably a non polar solvent.

The compound of interest may a lipophilic compound or a hydrophilic compound. If the compound of interest is a lipophilic compound, the layer may be hydrophobic layer impregnated with a non-polar solvent. Preferably, the non-polar solvent is octanol. If the compound is a hydrophilic compound, the layer may be hydrophilic layer impregnated with a polar solvent. Preferably, the non-polar solvent is water or a buffer.

In a preferred embodiment, the layer is attached at the bottom of a tube. The tube comprises but is not limited to, a cuvette, a well and a multiwell-plate. More preferably said hydrophobic layer is attached to a tube as described in European Patent Application EP 1232792 or in European Patent Application EP 05111522.8 which are herewith fully incorporated as reference. Preferred tubes are described in these documents.

Following materials are examples of materials which can be used to manufacture a tube: celluloseacetate, polycarbonate, polyvinylidene fluoride (PVDF), polysulfones, polystyrene, polypropylene (PP) or cyclic olefin copolymer (COC). Materials with similar shrinkage coefficient (in connection with injection molding) and melting properties may also be used for manufacturing a tube.

The method of the present invention allows a rapid determination of high lipophilicity values. In addition, less material has to be employed to test one compound and the method can be easily automated with standard liquid-handling workstation. Furthermore, no aqueous reference solutions with risk of precipitation are required.

Having now generally described this invention, the same will become better understood by reference to the specific examples, which are included herein for purpose of illustration only and are not intended to be limiting unless otherwise specified, in connection with the following figures.

EXAMPLES

Commercially available reagents referred to in the examples were used according to manufacturer's instructions unless otherwise indicated.

Example 1

Lipophilicity experiments were carried out in 96-deepwell microtiterplates in combination with the novel DIFI-tubes as described in the European patent application EP 1232792.

All compounds of the validation set were dissolved in dimethylsulfoxide at a concentration of 10 mM (DMSO-stock).

The experiment started with the accurate coating of 0,45 µm hydrophobic PVDF membranes (Immobilon-P PVDF (Millipore) and PVDF-Plus (Whatman, Headquater: 27 Great West Road, Brentford, Middlesex, TW8 9BW, UK), which were fixed on the bottom of the DI FI-tub es.

Each membrane is impregnated with exactly 1 µl octanol and 1µl DMSO-stock.

Figure 2:
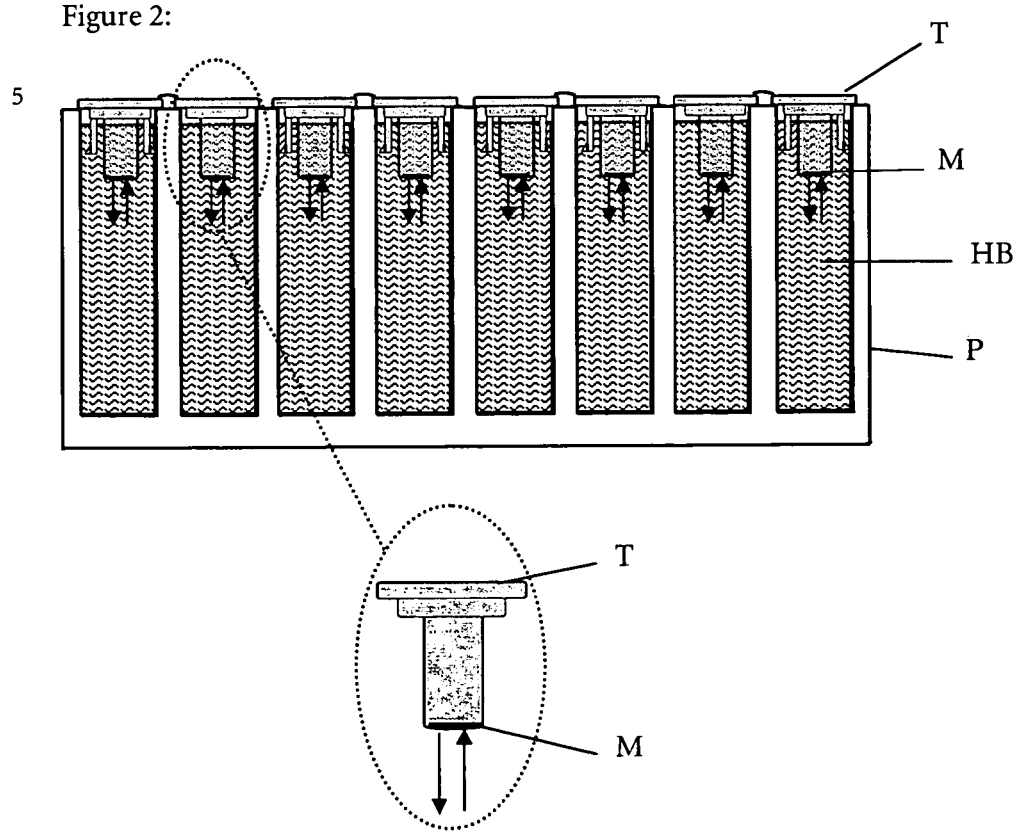
FIG. 2 shows schematically an embodiment of the method of the present invention. The membranes (M) are attached to tubes (T). The membranes are impregnated with octanol and the dissolved compound of interest is applied to the membrane. The tubes (T) are inserted in a plate (P) which is filled with a hydrophilic buffer (HB), whereby the membranes are in contact with the buffer. After reaching the equilibrium the tubes may simply be removed from the plate to get a separation of the phases.

After a short incubation of 10 min the tubes with the coated membranes were connected to a 96-deepwell plate which had been prefilled with exactly 1600 µl of the selected buffer solution (50 mM TAPSO (FLUKA, BioChemika, ArtNo.93357), pH 7.4). The resulting sandwich construct guarantees, that the membrane is completely dipped in the buffer solution (FIG. 2).

The plate was then sealed and shaken for two hours. During this time the substance was distributed between the membrane, the octanol and the buffer solution accordingly.

After the distribution equilibrium was reached (after 2 h) the tubes were carefully disassembled from the top of the deepwell plate in order to analyze the octanol phase which still stucks to the membrane.

Therefore, the remaining compound in the octanol phase was washed out with additional octanol as eluent. The concentration of the substance in the eluent was then determined by UV spectroscopy at absorption wavelengths between 250 and 450 nm.

In order to know the exact sample concentration before incubation with buffer a reference plate was generated under the same conditions as the described sample plate above. The reference plate was directly treated with the eluent and the resulted reference concentration in the octanol phase was measured by UV spectroscopy.

Evaluation

The lipophilicity value log D may be calculated from the analyzed sample concentration after incubation with buffer ($C_o$) and the reference concentration before distribution ($C_{ref}$).

$$\log D = \log\left(\frac{C_o}{C_{ref} - C_o} \cdot \frac{V_w}{V_o}\right)$$

Due to the fact, that all UV measurements were carried out under the same conditions, the concentration term were replaced by UV-absorption values (Abs) at the same wavelength.

$$\log D = \log\left(\frac{Abs_o}{Abs_{ref} - Abs_o} \cdot \frac{V_w}{V_o}\right)$$

In this equation, $V_w$ is the volume of the aqueous phase was divided by the volume of the octanol phase $V_o$.

Validation

A set of 14 well-characterized, chemically diverse drugs with known log D values from literature was used to validate this method. For each compounds three determinations were performed according to the described method above. The preparation of the reference and sample plate was performed manually.

Figure 3:
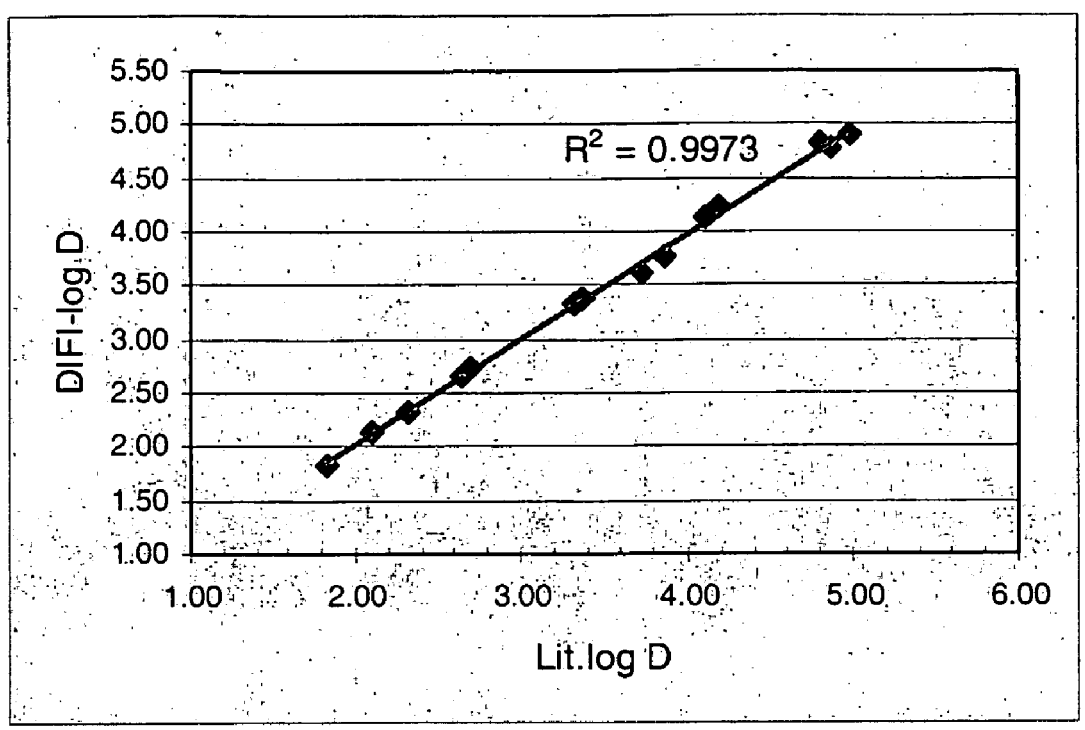
FIG. 3 shows a linear regression curve of log D obtained by the method of the present invention (DIFI-log D) and values from literature (Lit.log D). The literature values were found in MEDChem databases (commercial Database from DAYLIGHTChemical Information Systems Inc. 27401 Los Alto, USA), Winiwarter et al , J. Med. Chem, 41: 4939-49 (1998) and Sirius Technical Application Notes Volume 2 (1995).

The obtained log D values (DIFI-log D) were then compared with the values from ture (Lit.log D). Table 1 summarizes the results of the validation. Corresponding data were in FIG. 3.

TABLE 1

Validation set of 14 drugs with known log D values from literature (Lit. log D). A comparison of literature values from different sources with the data obtained by the new method validates the method of the present invention.

| No. | Compound | Lit. log D | Source | DIFI-log D |
|---|---|---|---|---|
| 1 | Astemizole | 4.10 | a) | 4.12 |
| 2 | Carvedilol | 3.37 | a) | 3.38 |
| 3 | Chlorprothixene | 4.19 | a)b) | 4.24 |
| 4 | Clotrimazole | 4.99 | a) | 4.91 |
| 5 | Dexamethasone | 1.83 | a) | 1.83 |
| 6 | Diltiazem | 2.32 | a)b) | 2.33 |
| 7 | Felodipine | 4.80 | a) | 4.84 |
| 8 | Imipramine | 2.65 | a) | 2.66 |
| 9 | Mitotane | 4.87 | a) | 4.78 |
| 10 | Nimodipine | 3.73 | a) | 3.61 |
| 11 | Progesterone | 3.87 | a) | 3.77 |
| 12 | Quinine | 2.10 | a) | 2.15 |
| 13 | Testosterone | 3.32 | a) | 3.33 |
| 14 | Verapamil | 2.70 | c) | 2.73 | a) MEDChem01, MEDChem03
b) calculated from logP and pKa
c) Winiwarter, S., Bonham, N. M., Ax, F., Hallberg, A., Lennernas, H., Karlen, A., J. Med. Chem., 41, 4939-4949 (1998)
d) Sirius Technical Application Notes Volume 2 (1995)

In comparison with the HTlog D the method of the present invention requires an extremely low octanol-water ratio for the determination of high log D values. Further advantages lies in the reduced sample consumption and in the easy separation of the octanol phase and the transfer of the carrier fixed non-polar solvent to multiple wells with polar solvent, thus increasing the distribution volume and therefore the measurement range for highly lipophilic compounds (Table 2).

TABLE 2

HTlog D in comparison to the new approach.

| | Required DMSO-stock with 10 mM1 (Without dead volume) | Analyzed phase | Octanol/Water ratio | Separation of the Octanol phase possible? |
|---|---|---|---|---|
| HTlog D | 32 µl | Water phase | 3/180 | NO |
| Method of the present invention | 6 µl | Octanol phase | 1/1600 (or multiple of the polar solvent volume e.g. 1/3200, 1/4800) | YES |

The invention claimed is:

1. A method for determining the lipophilicity of a compound of interest comprising
   a) impregnating a layer with a solvent A, wherein solvent A is polar or non-polar and wherein layer is made of a hydrophilic material if solvent A is polar and that the layer is made of hydrophobic material if solvent A is non-polar,
   b) applying the compound of interest on the impregnated layer,
   c) adding a solvent B, wherein solvent B is a polar solvent if solvent A is a non-polar solvent, and solvent B is a non-polar solvent if solvent A is a polar solvent,
   d) removing the solvent B after the distribution equilibrium has been reached, and
   e) determining the quantity of the compound of interest in at least one of the solvent phases.

2. The method of claim 1 wherein the quantity of the compound of interest is determined in phase sticking to the layer.

3. The method of claim 2 wherein the layer is a hydrophobic layer.

4. The method of claim 3 wherein solvent A is a non-polar solvent and the solvent B is a polar solvent.

5. The method of claim 4 wherein the non-polar solvent is octanol.

6. The method of claim 4 wherein the polar solvent is a buffer.

7. The method of claim 2 wherein the layer is a hydrophilic layer.

8. The method of claim 7 wherein the solvent A is a polar solvent and the solvent B is a non-polar solvent.

9. The method of claim 8 wherein the non-polar solvent is octanol.

10. The method of claim 8 wherein the polar solvent is a buffer.

11. The method of claim 1 wherein the layer is a membrane.

12. The method of claim 11 wherein the layer is attached to the bottom of a tube.

* * * * *